United States Patent
Hasselbrink et al.

(10) Patent No.: US 7,284,409 B2
(45) Date of Patent: Oct. 23, 2007

(54) THERMAL MODULATION FOR GAS CHROMATOGRAPHY

(75) Inventors: Ernest F. Hasselbrink, Londonderry, NH (US); Mark Libardoni, Ann Arbor, MI (US); Richard D. Sacks, deceased, late of Ann Arbor, MI (US); by Kristine Stewart, legal representative, Ann Arbor, MI (US); J. Hunter Waite, Dexter, MI (US); Bruce P. Block, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 173 days.

(21) Appl. No.: 11/070,796

(22) Filed: Mar. 2, 2005

(65) Prior Publication Data

US 2005/0247104 A1 Nov. 10, 2005

Related U.S. Application Data

(60) Provisional application No. 60/568,446, filed on May 5, 2004.

(51) Int. Cl.
*G01N 30/02* (2006.01)
(52) U.S. Cl. .................... 73/23.42; 73/23.35
(58) Field of Classification Search ............... 73/23.35, 73/23.41, 23.42
See application file for complete search history.

(56) References Cited

U.S. PATENT DOCUMENTS

| | | | |
|---|---|---|---|
| 4,863,493 A * | 9/1989 | Kotani et al. .................. 95/14 |
| 5,135,549 A | 8/1992 | Phillips et al. .................... 95/8 |
| 5,141,532 A * | 8/1992 | Sacks et al. .................... 95/87 |
| 5,196,039 A * | 3/1993 | Phillips et al. .............. 210/656 |
| 5,205,154 A | 4/1993 | Lee et al. |
| 5,288,310 A * | 2/1994 | Peters et al. .................. 96/104 |
| 5,492,838 A * | 2/1996 | Pawliszyn .................... 436/178 |
| 5,596,876 A * | 1/1997 | Manura et al. .............. 62/55.5 |
| 6,511,760 B1 | 1/2003 | Barone et al. |
| 6,974,528 B2 * | 12/2005 | Liu et al. .................... 204/456 |

OTHER PUBLICATIONS

Abstract, "Solutions In Gas Chromatography", Author Patrick J. Hunt, Co-Authors Charles Hasselbrink, Mark Libardoni, Richard D. Sacks, Pittcon, Mar. 8, 2004, p. 1.

Abstract, "Solutions In Gas Chromatography", Author Mark Libardoni, Co-Authors Megan McGuigan, Richard D. Sacks, Pittcon, Mar. 8, 2004, p. 1.

* cited by examiner

*Primary Examiner*—Daniel S. Larkin
(74) *Attorney, Agent, or Firm*—Harness, Dickey & Pierce, P.L.C.

(57) ABSTRACT

A thermal modulator device for gas chromatography and associated methods. The thermal modulator device includes a cooling member, an electrically conductive capillary in direct thermal contact with the cooling member, and a power supply electrically coupled to the capillary and operable for controlled resistive heating of the capillary.

8 Claims, 9 Drawing Sheets

Fig-1A

Thermal Modulator

THERMAL MODULATION FOR GAS CHROMATOGRAPHY

CROSS-REFERENCE TO RELATED APPLICATIONS

This application claims the benefit of U.S. Provisional Applications No. 60/550,869, filed on Mar. 5, 2004, and No. 60/568,446, filed on May 5, 2004. The disclosure(s) of the above applications are incorporated herein by reference.

STATEMENT OF GOVERNMENTAL SUPPORT

This invention was made with Government support under Grant No. NAG5 12171 and sub-contract No. 1232378 awarded by the Jet Propulsion Lab (NASA). The government has certain rights in this invention.

FIELD OF THE INVENTION

The present invention relates to gas chromatography and, more particularly, relates to an apparatus and method of using the same capable of achieving fast-response control of the temperature of metal capillaries in gas chromatography applications.

INTRODUCTION

Traditional gas chromatography (GC) is one of the most widely used methods for analysis of chemical compounds, and is used in a variety of applications, such as engine exhaust gas monitoring, environmental monitoring, forensics, and industrial process monitoring. In traditional gas chromatography a small sample of analyte vapor is introduced into a small capillary ("column") amidst a continuous flow of "carrier gas", usually either hydrogen or helium. The capillary has a thin-film coating on its inside wall. The coating is known as a "stationary phase", and is such that which different compounds have different affinity with the stationary phase. Various chemical components of the sample gas move at different average speeds through the small capillary because of their different affinities for the stationary phase. As they exit the column at the end, these (ideally) separated compounds can be detected with a variety of detectors, such as a flame ionization detector or time-of-flight mass spectrometer.

It can be difficult to separate components with similar affinities for a given stationary phase, because they move at similar speeds through the column. For this reason, a relatively recent modification of this approach, known as two-dimensional gas chromatography, "2DGC" or "GC-GC", attempts to separate compounds using two capillaries in series, each coated with a different stationary phase, so that compounds with similar affinities for the first stationary phase can then be separated by differential affinity in the second column. It is, however, possible that separated bands from the first column could subsequently overlap after passing through the second column. For this reason, known devices for trapping and accumulating gases from the first column while conducting an analysis in the second column are used. Such devices include, for example, means disclosed in U.S. Pat. Nos. 5,135,549, 5,196,039, and 5,205,154, which are incorporated herein by reference. Such devices are known as thermal modulators, as they utilize heating and cooling of a short segment of capillary ("modulated column segment" or "column" for short) to achieve momentary trapping of analyte.

In general, these thermal modulators vary the temperature of the modulated column section in the following exemplary cycle: maintain the column at a low temperature of 0° C. to −40° C. for a period of 1-10 seconds to accumulate the analyte from the first column within the thermal modulator; heat in tens of milliseconds or faster the modulated column section to 100° C.-350° C.; maintain this temperature for 10-200 milliseconds to allow the analyte to be injected into the second column in a narrow pulse tens of milliseconds wide; cool the modulated column section rapidly, in less than 200 milliseconds preferably, back to a low temperature, preferably below 0° C., as performance improves with lower temperature. The degree to which this heating and cooling profile can be exactly controlled can have significant effects on performance, because of an exponential dependence of gas elution speed on modulator temperature.

There are known disadvantages of the existing modulator devices and methods. For example, some known methods require moving heated parts or alternating introduction of strong blasts of cold and hot gases over the modulated column segment. Known electrically heated thermal modulators require significant air or other gas flow to cool them quickly enough for practical use. Commercially-available 2DGC systems typically using the cooling-gas method rely on large volumes of cold nitrogen (supplied as liquid nitrogen supplied in large cumbersome dewars) for cooling, and heated air (drawing large amounts of electric current for heating) for heating the modulated column section. The high draw of power and liquid nitrogen for this thermal modulation method makes portable (or other low-power, lightweight) embodiments of 2DGC impractical or impossible. Further, heating and cooling small objects, such as a modulated column section, by convective flow of gases is very inefficient and slow. Known thermal modulation methods that employ convective gas cooling may require a very high flow rate of gases at very cold or cryogenic temperatures.

SUMMARY OF THE INVENTION

The present teachings provide a thermal modulator device that includes a cooling member, an electrically conductive capillary in direct thermal contact with the cooling member, and a power supply electrically coupled to the capillary and operable for controlled resistive heating of the capillary.

The present teachings also provide a method for temperature modulation in gas chromatography. The method includes providing an electrically conductive capillary, chilling the capillary by direct thermal contact with a cooling member, and coupling the capillary to an electric power supply for resistive heating.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of the various embodiments is merely exemplary in nature and is in no way intended to limit the invention, its application, or uses.

The present teachings provide devices and associated methods for achieving rapid and efficient thermal modulation of the capillary for two-dimensional gas chromatography (2DGC). The present teachings are also applicable to sample pre-concentration in both single column and 2D gas chromatography. In one aspect, the present teachings provide a thermal modulator device for gas chromatography. The thermal modulator device includes a cooling member and an electrically conductive capillary in direct thermal contact with the cooling member. The cooling member can be a liquid coolant or a solid coolant. A power supply 190 (shown in FIG. 1B) operates for controlling resistive heating of the capillary.

Figure 1A:
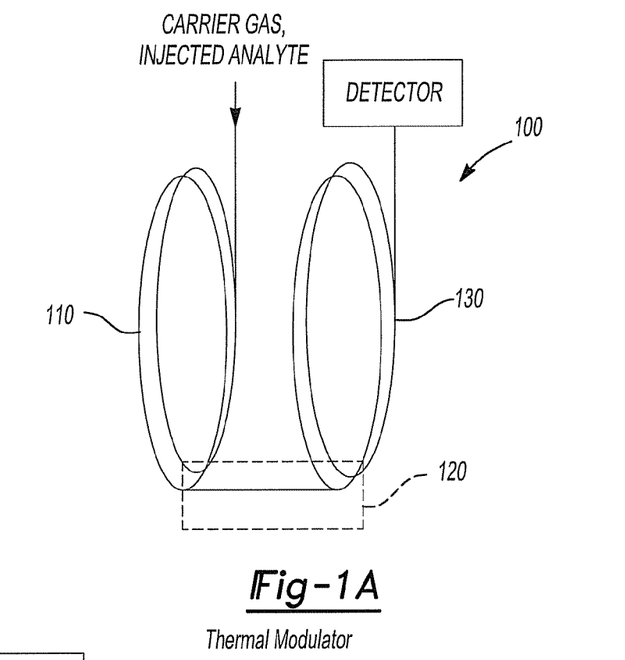
FIG. 1A illustrates an outline of a thermal modulator device according to the present teachings, shown in a schematically illustrated 2DGC apparatus.
Figure 7:
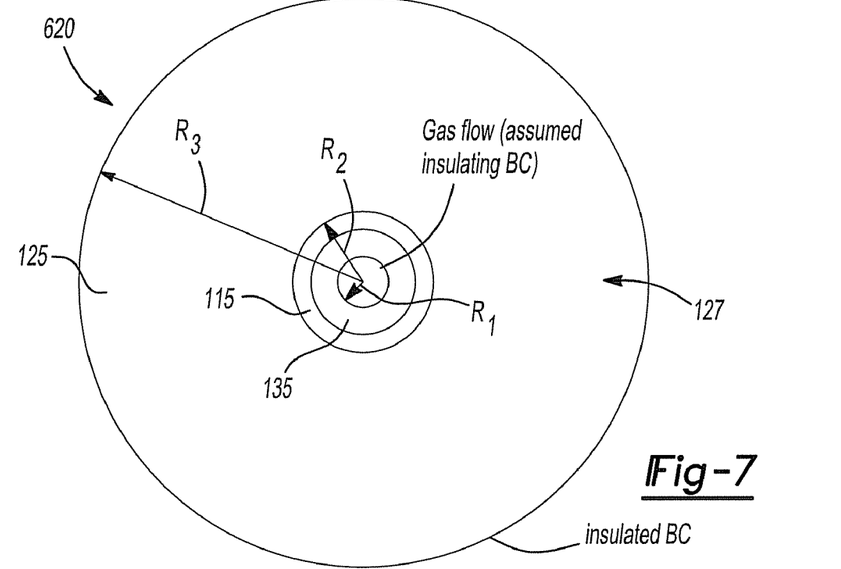
FIG. 7 is a sectional view of an exemplary thermal modulator device employing a solid coolant according to the present teachings.
Figure 11:
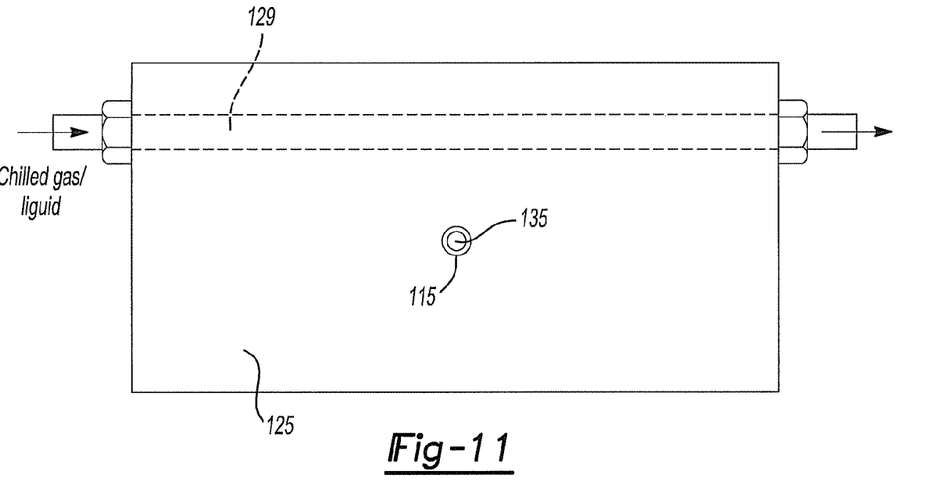
FIG. 11 illustrates a sectional view of an exemplary thermal modulator device employing a solid coolant according to the present teachings.
Figure 12:
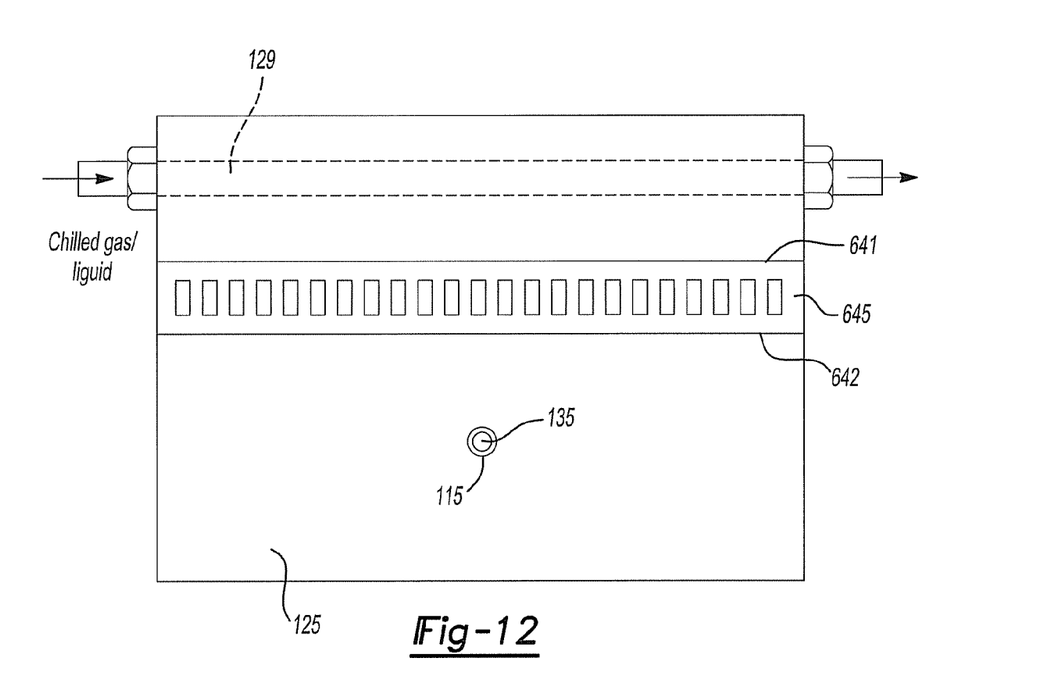
FIG. 12 illustrates a sectional view of an exemplary thermal modulator device employing a solid coolant according to the present teachings.

Referring to FIG. 1A, a thermal modulator device 120 is schematically illustrated in the environment of a typical two-dimensional gas chromatography (2DGC) apparatus 100, according to the present teachings. As will be discussed below, various exemplary illustrations of the thermal modulator device 120 employing a liquid coolant are provided in FIGS. 1B, 3A, 3B, 5A and 5B. Exemplary illustrations of the thermal modulator device 620 employing a solid coolant 127 are shown in FIGS. 7, 11, and 12.

Throughout the written description of the invention, the terms "modulator" and "modulated column section" may be used interchangeably. The terms "column" and "capillary" are also used interchangeably, since nearly all modern-day gas chromatography is conducted using capillaries that are popularly referred to as columns.

Figure 1B:
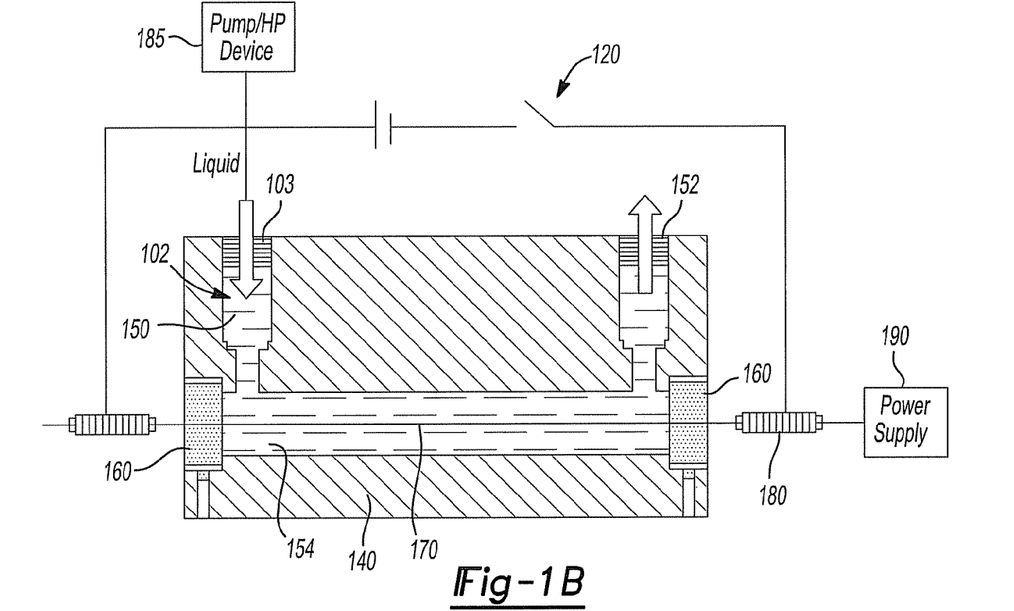
FIG. 1B is a sectional view of an exemplary thermal modulator device according to the present teachings.

Referring to FIGS. 1A and 1B, the exemplary 2DGC apparatus 100 includes first and second chromatographic columns 110, 130, and an exemplary thermal modulator device 120 of the present teachings connected in series. The thermal modulator device 120 comprises modulated column section capillary 170 (shown in FIG. 1B) which can be chilled and heated according to the present teachings. The capillary 170 is electrically conductive. Bands of analyte separated in the first chromatographic column 110 are adsorbed into the capillary 170 when the capillary 170 is chilled, then quickly desorbed by rapid heating so as to allow a concentrated band of analyte to enter into the second chromatographic column 130, where they are separated.

Referring to FIG. 1B, one aspect of the thermal modulator device 120 is illustrated for a cooling member 102 which is a liquid coolant 103. The liquid coolant 103 can be moving, as illustrated in FIG. 1B, or static. In the absence of flow, conductive heat transfer can be sufficient for cooling. The thermal modulator device 120 can include a housing 140 having inlet and outlet ports 150, 152. The moving liquid coolant 103 flows into inlet port 150, through bath 154 and out of the outlet port 152. The capillary 170 can be supported by the housing 140, immersed in the bath 154. The liquid coolant 103 can be moving by known means 185, such as pumping device or by hydrostatic pressure device, for example. Further the liquid coolant 103 may be moving by natural convection, such as by density gradients and gravity. The flow of the moving liquid coolant 103 can be in a co-flowing configuration, illustrated in FIG. 1B, or in a cross-flowing configuration, illustrated in FIGS. 5A and 5B. Seals 160 at the ends of the bath 154 allow the capillary 170 to pass through the housing 140 without cooling leakage. Electrical power is applied to the capillary 170 in brief periods, through ohmic connections 180, which may be comprised of commercially-available column connectors, or may be soldered or silver-soldered connections, or any other known connectors. Stationary phase in the portion of the column within these connectors is typically removed to minimize adsorption at any temperature.

Figure 2A:
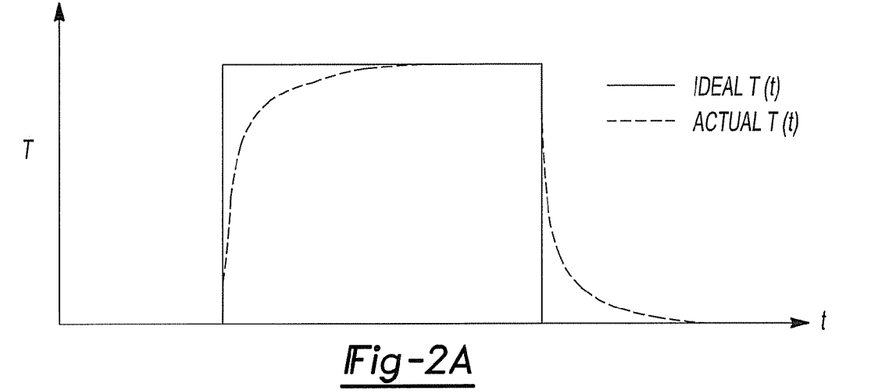
FIG. 2A illustrates idealized and actual temperature versus time profiles for a thermal modulator according to the present teachings.
Figure 2B:
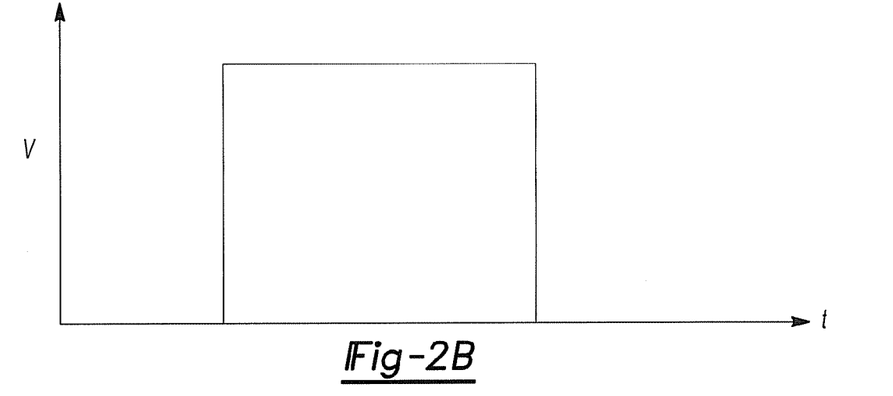
FIGS. 2B and 2C illustrate voltage profiles corresponding to the idealized and actual temperature versus time profiles of FIG. 2A.
Figure 2C:
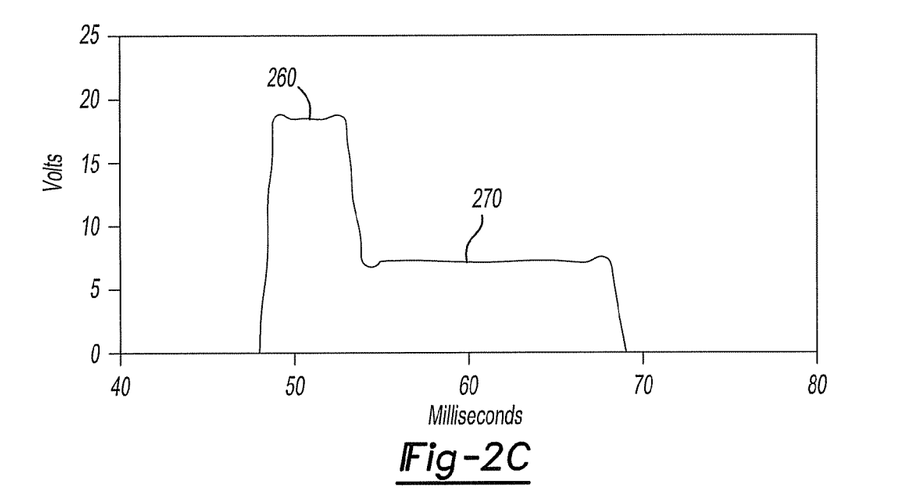

Referring to FIGS. 2A-2C, an idealized temperature versus time profile for the thermal modulator device 120 is illustrated in FIG. 2A in solid line. An applied voltage profile that can be used to approximate the idealized temperature is shown in FIG. 2B. The actual temperature profile corresponding to the voltage profile of FIG. 2B is illustrated with a dotted line in FIG. 2A and may exhibit an exponential response of the temperature which only asymptotically approaches its maximum heating temperature during heating. To improve or remedy this condition, a two-step voltage program illustrated in FIG. 2C can be used. The voltage program includes an "initial voltage" 260 and a "maintenance" voltage 270.

The power dissipated in the modulated column section is proportional to the square of the voltage applied, and inversely proportional to the resistance of the modulated column section. The initial voltage 260 is preferred to be as high as practically possible for rapid temperature rise. Because of large current requirements, a capacitive discharge power supply may be advantageous, but commercially available DC or AC power supplies can be more than adequate. For very short times, before appreciable heat transfer to the liquid can occur, the rate of temperature rise is proportional to input power and inverse to the thermal capacity (mass times heat capacity) of the modulated column section. After some time, however, the rate of temperature rise decreases due to convective and conductive losses to the cooling fluid, and a steady-state temperature is achieved. The time for this to occur is proportional to the square of the thermal boundary layer thickness (about half the diameter of the capillary) at a cross flow Reynolds number of unity and inversely proportional to the thermal diffusivity of the liquid. For example, for water, and a 0.36 millimeter diameter capillary at unity Reynolds number, this time is approximately 210 milliseconds, and is much longer than the 10 millisecond or so desired rise time for the modulated column section temperature, so the temperature rise is approximately linear during this time. Therefore, relatively little heat is lost in the 10 millisecond heating period, but significant heat loss will occur over a 200 millisecond period even at a very low flow speed. Accordingly, if it is desired to maintain the temperature longer than a few tens of milliseconds, the temperature can be maintained by application of the maintenance voltage 270. The required maintenance voltage 270 depends on the exact flow speed across the thermal modulator device 120 as well as the fluid composition and temperature and the desired temperature of the thermal modulator device 120. Because these variables may not always be well controlled, and most stationary phases can be adversely affected by excessively high temperatures, it may be desirable to monitor the temperature of the modulated column section by known methods.

In one exemplary aspect, a metal capillary 170 can be used. The metal capillary 170 can be typically coated in its interior with a passivating layer of silica, glass, or similarly nonreactive material, and additionally with a thin film of any of a plurality of commercially available wax or polymer stationary phases. One commercially available metallic capillary that can be used is the Silco-Steel™ capillary available from Restek Corporation, Bellefonte, Pa., but any capillary with appropriate passivating layer can be used. The use of a metal capillary aids the mechanical integrity of the device while providing a path for electrical conduction, as well as rapid thermal conduction radially inward to the stationary phase and to the gas within the capillary. It will be appreciated, however, that the present teachings are not limited to the use of steel capillaries, and practically any metal can be used. In particular, metals with resistance to thermal fatigue (such as steel or nickel-chromium) and metals with large changes in electrical resistivity over the temperature range of interest can be preferentially used. Further, capillaries of any length (typically 0.1 to 20 centimeters), or any practical diameter (from 2 millimeters down to 10 micrometers) can be used.

Figure 3A:
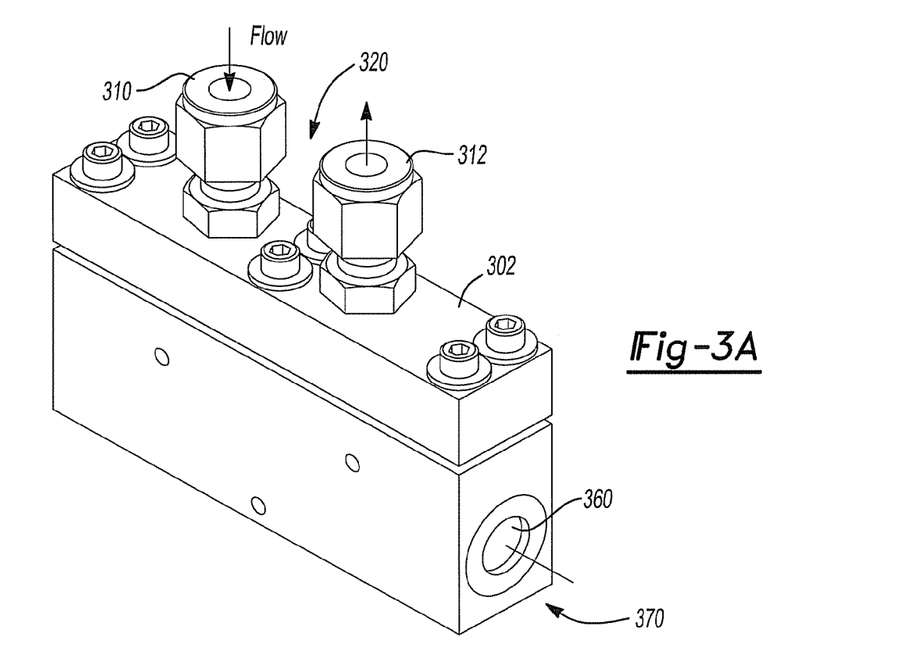
FIG. 3A is a perspective view of an exemplary two-stage thermal modulator device according to the present teachings.
Figure 3B:
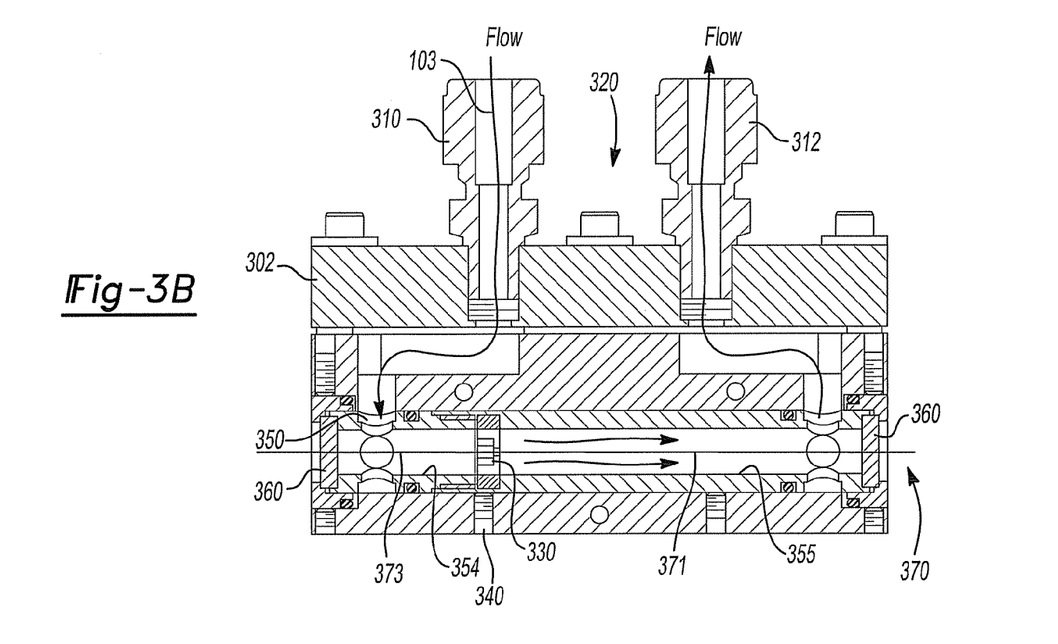
FIG. 3B is a sectional view of the two-stage thermal modulator of FIG. 3A.

Referring to FIGS. 3A and 3B, a "two-stage" thermal modulator device 320 utilizing direct-liquid-immersion for heat transfer is illustrated according to the present teachings. The thermal modulator device 320 includes a housing 302 and two external inlet and outlet ports 310, 312. Two capillary segments 371, 373 of an electrically conductive capillary 370 can be independently heated by voltages applied to external connectors at the ends of the housing 302. Current returns to a power supply through a center-tapped ground electrically connected to the capillary via a copper disk 330 soldered to the capillary 370, defining baths 354, 355. The copper disk 330 connects to the housing 302 with a set screw 340, and the housing 302 is connected to earth ground by an external connection (not shown). The copper disk 330 includes through-holes in its face so that the liquid coolant 103 may optionally be passed through both baths 354, 355 and through the external inlet and outlet ports 310, 312 as illustrated by arrows in FIG. 3B. Flow out of the ends of the housing 302 can be prevented, for example, by a septum 360 held in place with mechanical press-seals, which allow the capillary to pass through, or other known devices.

In another aspect, the liquid coolant 103 is used in a non-moving static or stationary arrangement, and is not passed through the inlet and outlet ports 310, 312 in a moving flow. The baths 354, 355 can be filled with the liquid coolant 103, and the capillary 370 is immersed in this static liquid coolant 103. Chilling of the static liquid coolant 103 can be achieved by conduction. For example, the housing 302 can be chilled by any of a variety of known devices and methods, such as, for example by circulated or impinging cold liquid or gas or refrigerant, by contact with dry ice, liquid nitrogen, or by contact with a refrigeration device, such as a mechanical refrigerator or thermoelectric device. Stationary liquid can be effectively used in gas chromatography applications, for example, when the gap between the inner wall of the housing 302 and the outer wall of the capillary 370 is about 0.45 millimeters. However, owing to the exponential dependence of retention factor on temperature, larger tolerances are possible as long as excessive overheating of the capillary 370 is avoided during the heat-up phase, because only a modest amount of cooling is then necessary to begin trapping again.

Figure 4:
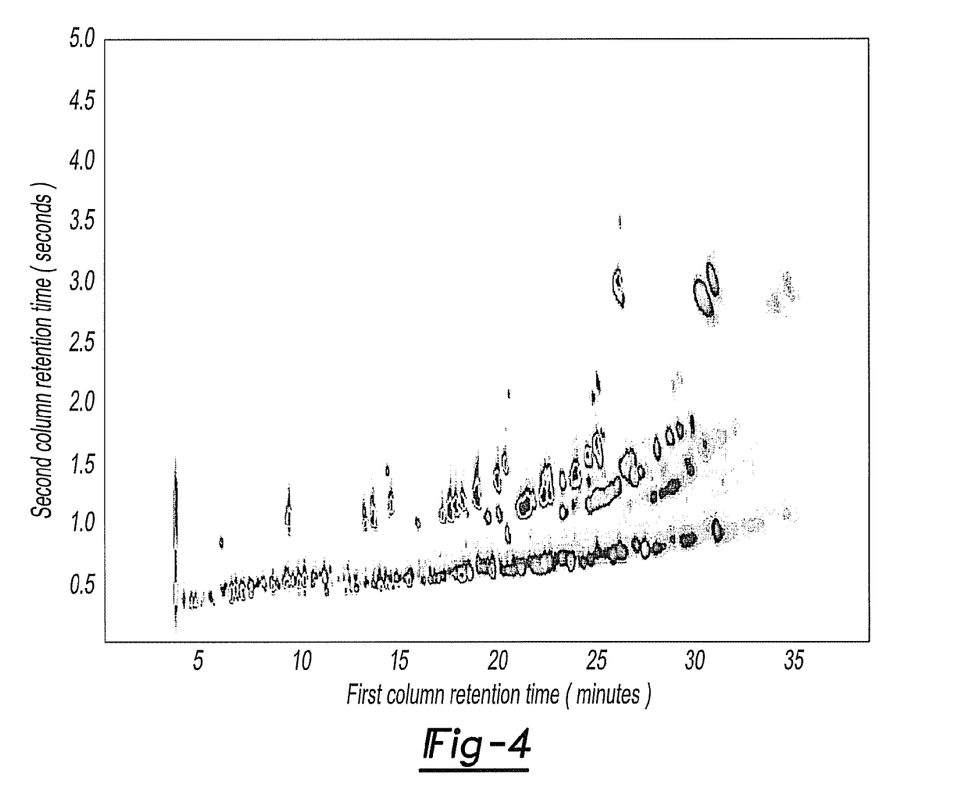
FIG. 4 illustrates an exemplary two-dimensional chromatogram obtained according to the present teachings.

Referring to FIG. 4, a representative two-dimensional chromatogram obtained according to the present teachings is illustrated. The data are obtained from samples of gasoline using a 30 m first column, 8 centimeter long modulated column section capillary comprised of Silco-Steel™ from Restek Corporation, and 1.5 meter long second column with a flame ionization detector. Flowing ethylene glycol is the liquid coolant, and the capillary was resistively pulse-heated every five seconds.

Figure 5A:
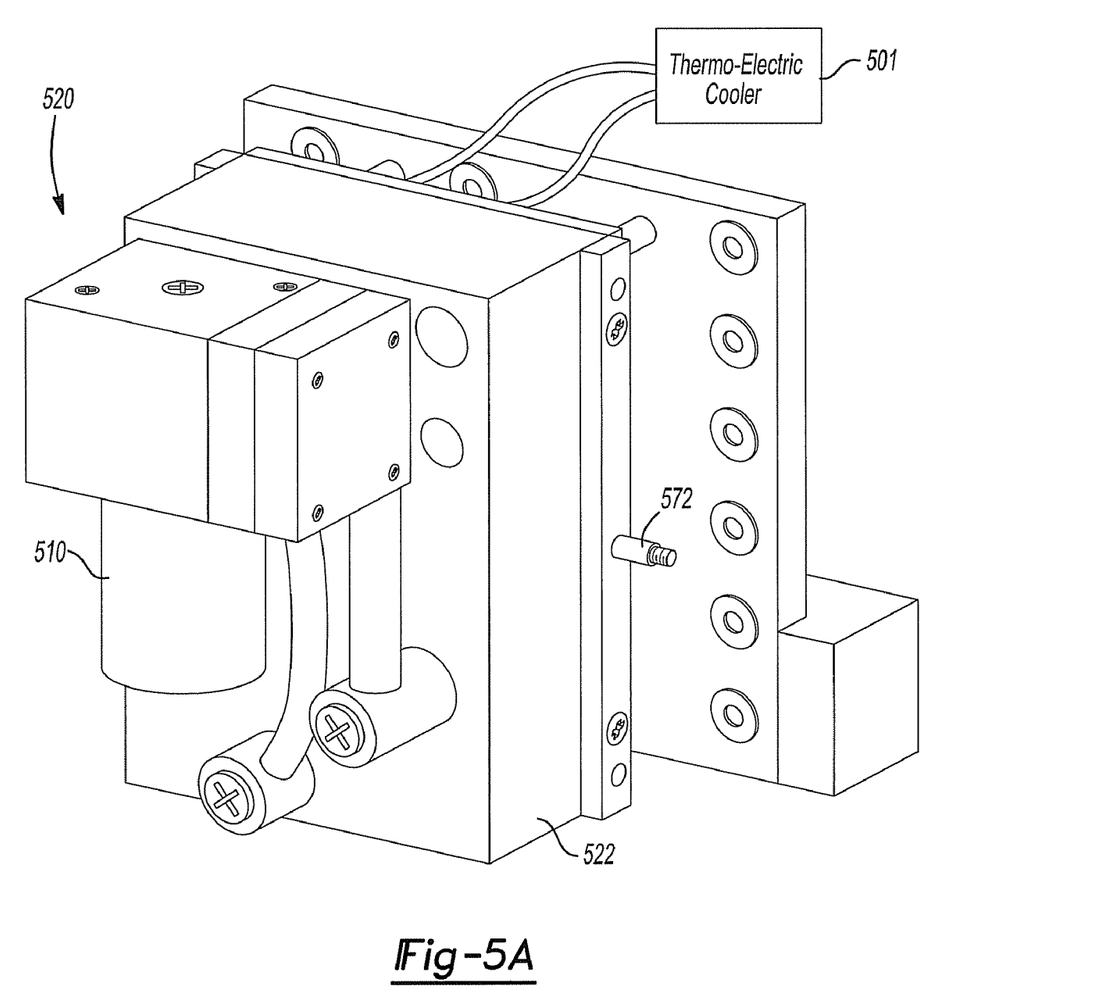
FIG. 5A is a perspective view of an exemplary thermal modulator device according to the present teachings, the device employing a cross-flowing arrangement.
Figure 5B:
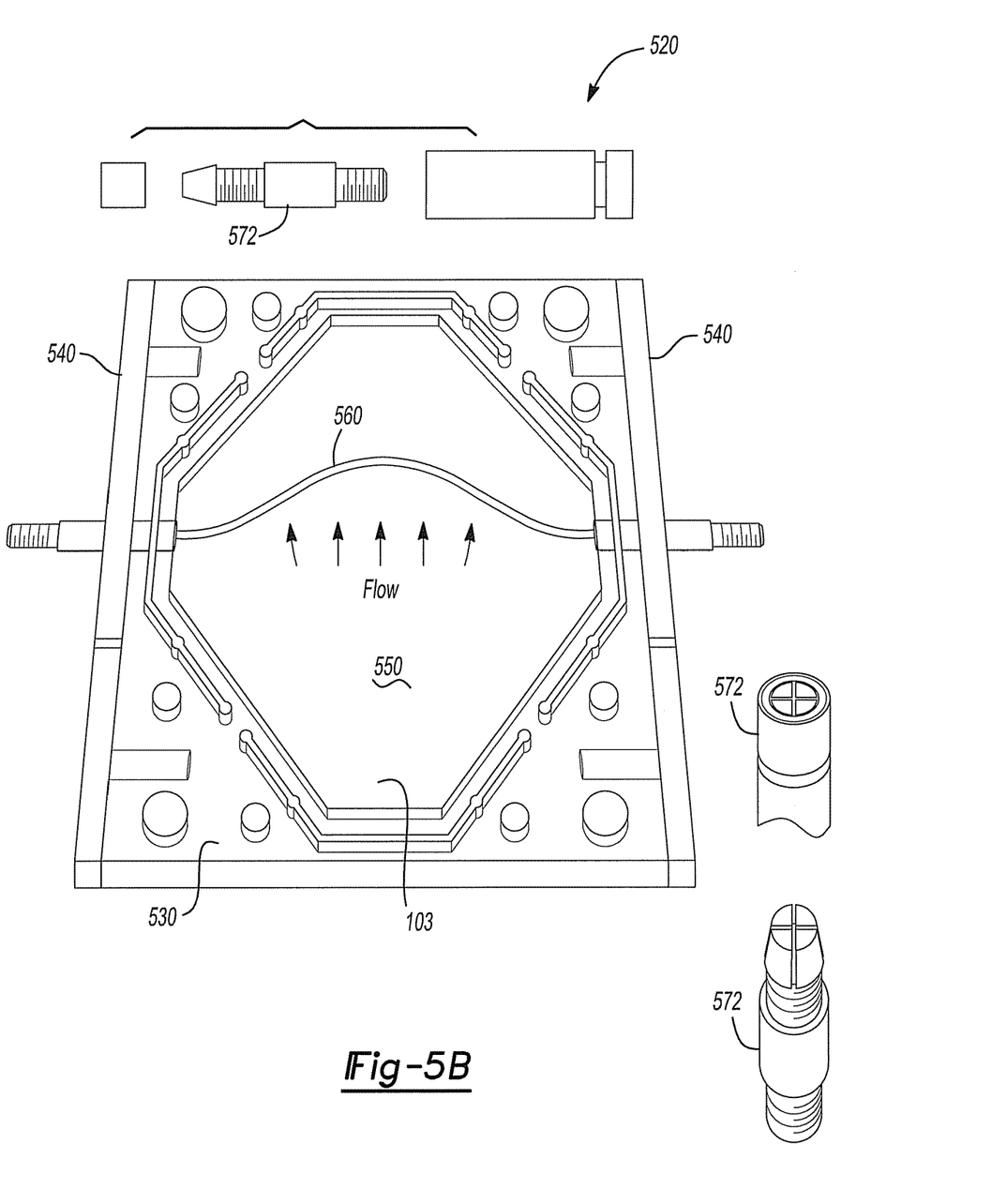
FIG. 5B is a partially exploded view of internal parts of the thermal modulator device of FIG. 5A.
Figure 6:
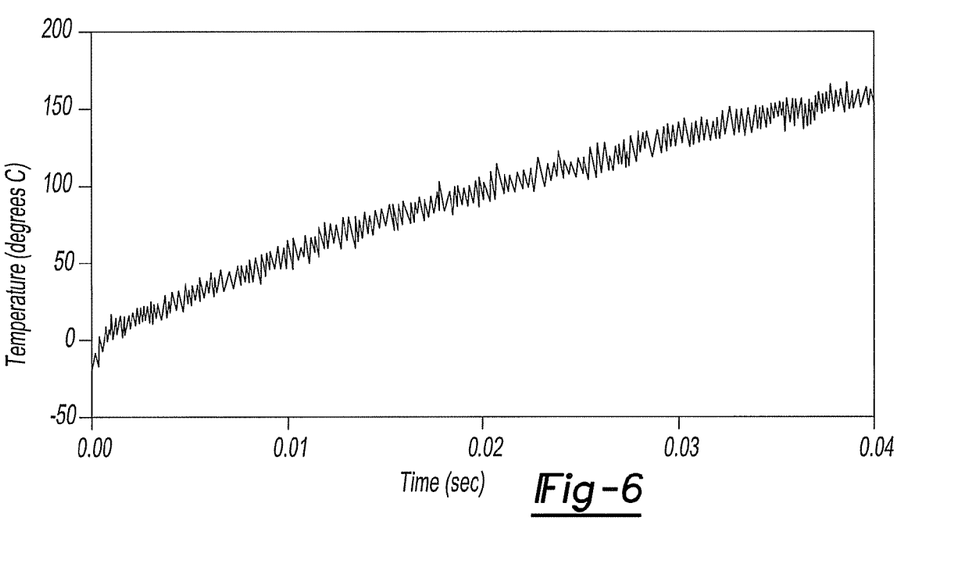
FIG. 6 illustrates a measured profile of temperature versus time in a resistively heated modulator immersed in static chilled liquid.

Referring to FIGS. 5A and 5B, an integrated single-stage thermal modulator device 520 utilizing direct-liquid-immersion for heat transfer is illustrated according to the present teachings. A thermoelectric refrigerator/cooler or Peltier stack 501 (not visible, but schematically shown in FIG. 5A) can be used to chill liquid coolant 103 re-circulated by an integrated miniature pump 510. The cold side of the thermoelectric cooler 501 is in contact with a wide flat cavity 550 defined within a plate 530 sandwiched between other sealing surfaces through which fluid may optionally flow. Liquid coolant 103 can be introduced into the cavity through a manifold 522 and flows over a conductive capillary 560 in a cross-flowing arrangement. This cross-flowing arrangement can improve heat transfer at low flow rates. Heat pumped out of the re-circulated (or static) liquid coolant 103 by the thermoelectric cooler 501 is rejected using a copper heat exchanger, which transfers the heat to tap water which is passed through it and sent to a drain. In one aspect, the column spans the width of the cavity 550, fastened to its ends electrical connectors 572, which can be custom-made to prevent leakage of the liquid out of the cavity 550. Electrical current is directed through the connectors 572 via conducting bus bars 540 that facilitate external connection to a power supply. Referring to FIG. 6, a measured profile of temperature versus time in a resistively heated modulator immersed in static chilled liquid is illustrated.

The required maintenance voltage depends on the exact flow speed across the modulator as well as the fluid composition and temperature and the desired temperature of the modulator. Because these variables may not always be well controlled, and most stationary phases can be adversely affected by excessively high temperatures, monitoring temperature of the modulated column section is desirable. A convenient means for doing so is to rely upon the fact that many metals (such as steel and platinum) have reasonably large and repeatable changes in resistivity between 0° C. and 250° C. (an approximate temperature range of interest for thermal modulation applications). This dependence can be monotonic and nearly linear. A fast in-situ two-point calibration (first at room temperature, and then at the chilled temperature) is within the purview of a person of ordinary skill in the art. The measurement can also be performed very quickly (in microseconds) so that, should the peak temperature be too high or too low, the power applied may be adjusted immediately.

Referring to FIGS. 7, 11 and 12, exemplary thermal modulator devices 620 operating with a solid coolant 127 with conduction heat transfer (in the absence of natural convection). Referring to FIG. 7, an electrically conductive modulated column segment capillary 135 can be surrounded by one or more layers of solid material 115 which place it in direct thermal contact with a relatively large solid mass 125, which can be conductive. The solid mass 125 can be maintained at low temperature by a chilled liquid running directly through it, or by an optional thermoelectric device which may have a liquid or air heat exchanger on its heated side, or is otherwise cooled by a plurality of standard means including a secondary thermoelectric device, an adiabatic expansion (Joule-Thompson) refrigerator, or a closed-loop refrigeration system, for example.

The momentary application of electric current pulses through the capillary 135 introduces a relatively small amount of average heating in the solid mass 125 compared to the rate at which heat is on average removed from the solid mass, and thus the solid mass 125 serves as a low temperature thermal sink that provides repeatable heat removal characteristics.

The solid material 115 between the modulated column and solid mass is optional. The solid material 115 can preferably be an electric insulator when the solid mass 125 is an electrical conductor. The thickness of the solid material 115 is chosen so that the product of its thermal resistance, and the thermal capacity of the capillary 135, yields a cooling time constant that is rapid enough for efficient modulation (less than 500 milliseconds). However, it should not be so thin that most of the power deposited into the capillary 135 is too rapidly lost into the solid mass 125.

Figure 8:
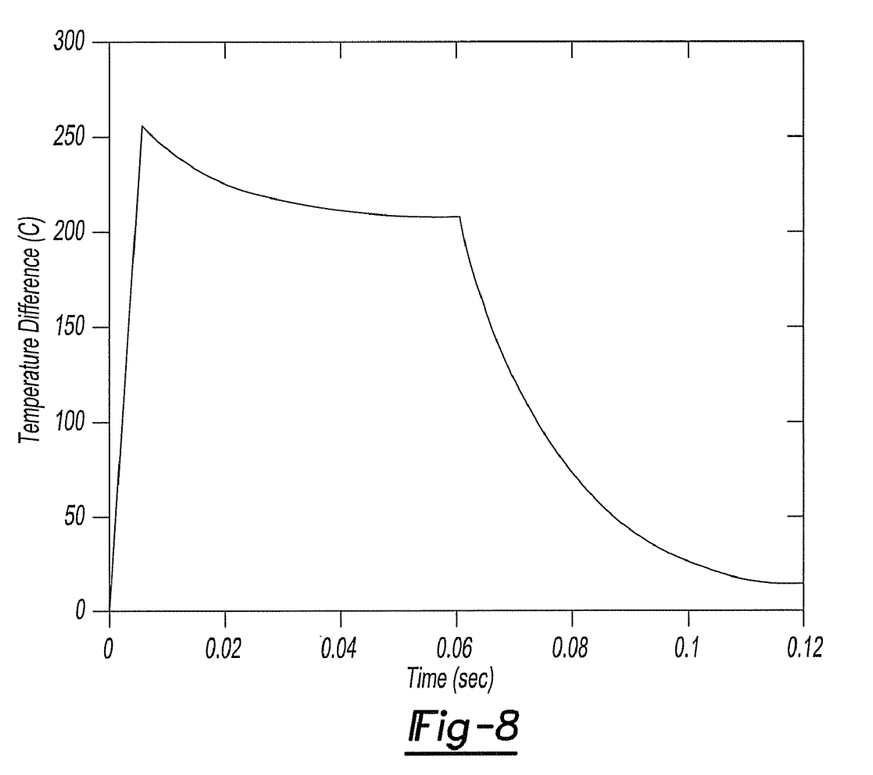
FIG. 8 illustrates an exemplary computed profile of temperature at a stationary phase versus time for a thermal modulator device employing a non-moving according to the present teachings.
Figure 9:
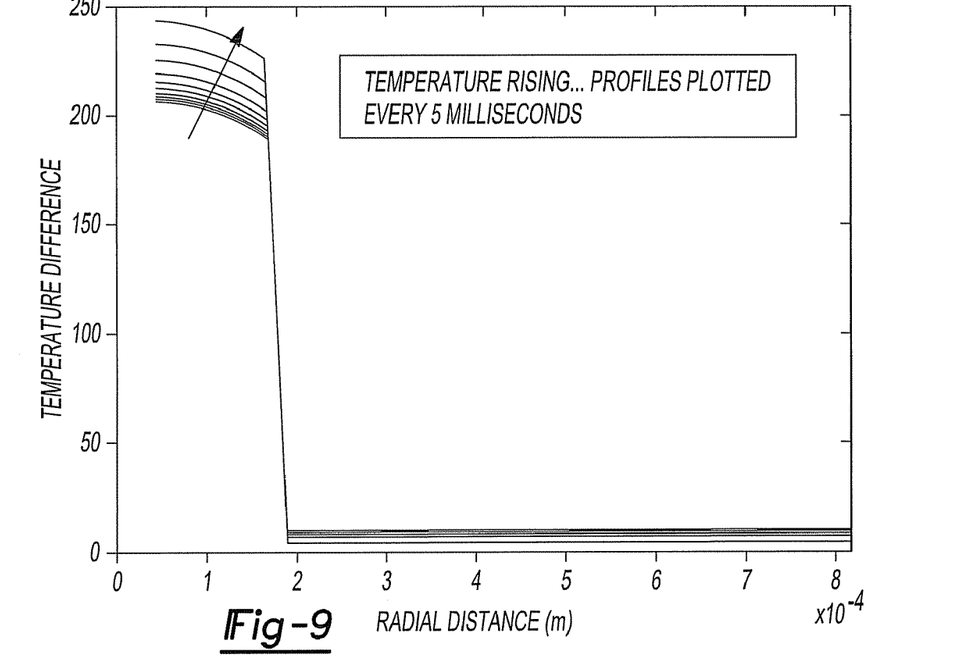
FIG. 9 illustrates detailed temperature profiles in a radial direction during a heating phase for thermal modulator device employing a solid coolant according to the present teachings.
Figure 10:
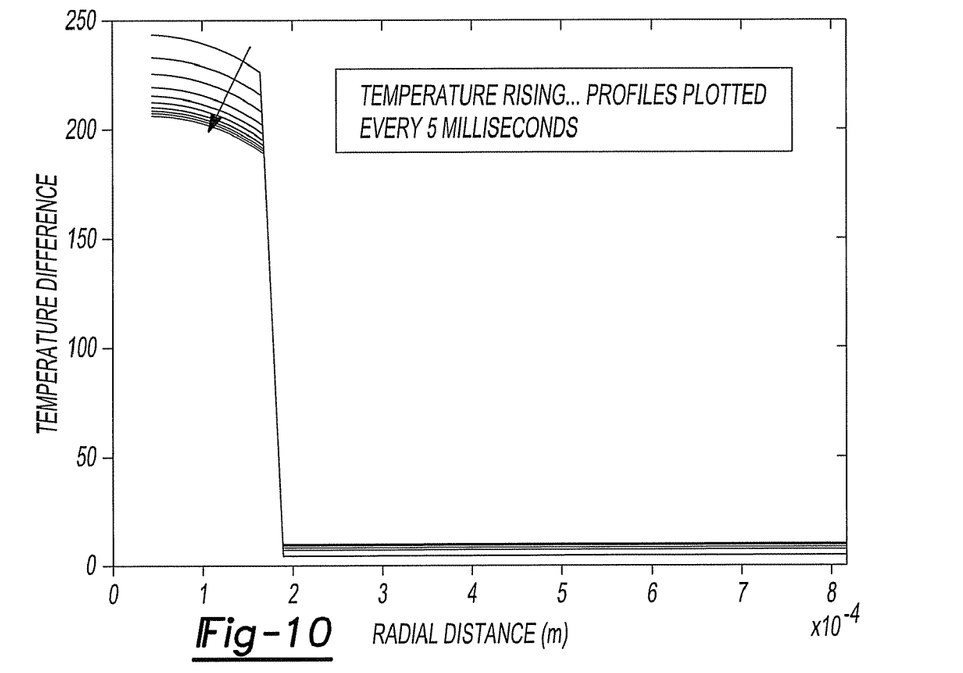
FIG. 10 illustrates detailed temperature profiles in a radial direction during a cooling phase for thermal modulator device employing a solid coolant according to the present teachings.

FIGS. 8-10 show computed results of an exemplary thermal modulation according to the present teachings. In this example, a 304 Stainless Steel capillary 135 of inner radius R1=50 microns and outer radius R2=170 microns is coated with a solid material 115 which is a film of polyimide about 30 microns thick. The film is in direct thermal contact by way of some thin conductive paste, grease, cement, or other compound with a solid mass 125 that has a large outer radius R3, which is large enough that its dimension is actually unimportant over the time scale of modulation. In this example, the solid mass 125 is a copper heat sink that has radius R3 greater than 4 mm. The results are obtained using tabulated properties and conservation of energy equations for radially-symmetric heat transfer. The conservation of energy equation for such a case, allowing for volumetric ohmic heating, is $(\rho c)\partial T/\partial t = \nabla \cdot (k \nabla T) + \sigma E^2$. Here $\rho$ is density, c is specific heat, T is temperature, t is time, k is thermal conductivity, $\sigma$ is electrical conductivity, and E is the applied electric field through the metallic capillary 135. This is an exact physical law, and any inaccuracies in applying these equations stem from not accounting for the geometry or material properties exactly, but generally it is widely accepted that simulation of conduction problems in heat transfer of this type can be performed with great accuracy using a proper numerical algorithm and sufficient spatial and temporal resolution. The computations are performed with a numerical algorithm with 4 micron or better spatial resolution, and 0.1 microsecond or better temporal resolution, according to conventional practice in the art. The capillary is 0.06 m long, and is heated by a 18 volt pulse, until t=6.4 milliseconds, then a 11.5 volt pulse until t=60 milliseconds. Cooling at later times is via conduction. Characteristic cooling time (1/e) is approximately 20 msec.

FIG. 8 illustrates the temperature at the inside wall of the thermal modulator device as a function of time. Detailed temperature profiles in the radial direction during the heating phase (the first 60 milliseconds of the simulation) are shown in FIG. 9. Temperature gradients are almost completely confined to the thin layer of polyimide, and that the copper heat sink (r>180 microns) is barely heated due to its large thermal capacity and the short timescale of the temperature pulse.

Detailed temperature profiles in the radial direction during the cooling phase after the first 60 milliseconds are shown in FIG. 10. Profiles are plotted every 5 milliseconds, from t=60 msec to t=120 msec. The copper heat sink (r>180 microns) is barely heated due to its large thermal capacity. If a 1 kilogram or larger copper heat sink is very well insulated from ambient conditions, it can be chilled prior to running the chromatogram, for example, in a freezer, and then operated without any active cooling system. The thin layer of thermal resistance of the solid material 115 is responsible for most of the temperature drop.

Known commercial devices use high-speed jets of cold gas to cool the heated modulator. The methods and devices according to the present teachings chill the thermal modulator capillary back to low temperature without using a consumable gas (typically liquid nitrogen), and avoids the associated cryogenic handling hardware that occupies significant space.

A variety of methods and devices can be used to keep the solid mass 125 continuously chilled. Two examples are illustrated in FIGS. 11 and 12. Referring to FIG. 11, the solid mass 125 is chilled directly by passing chilled gas (such as a cryogenic gas) or chilled liquid through the solid mass 125 through one or more passageways, or over one or more radiative fins on the surface or other direct chilling device 129. If the solid mass 125 has high thermal conductivity, this type of external cooling will make the solid mass essentially isothermal, at a temperature very near that of the supplied gas or chilled liquid. The gas can be chilled, for example, by expanding it from high to low pressure or by other known methods.

Referring to FIG. 12, a thermoelectric device 645 (Peltier stack) is used. A cold side 642 of the thermoelectric device 645 is in thermal contact with the solid mass 125, while a hot side 641 of the thermoelectric device 645 dissipates heat uses a direct chilling device 129, such as a gas or liquid heat exchanger, or fins. For example, lab water at 25 degrees centigrade can be supplied to efficiently remove heat from the hot side 641 of the thermoelectric device 645, while the cold side 642 can be maintained at −50° C. or lower temperature using commercially available Peltier stacks. Adequate heat transfer characteristics can also be achieved by using convective cooling from fins using a fan blowing room air across them.

According to the present teachings, fast-response control of the temperature of one or more modulated column sections or capillaries can be achieved by chilling through immersion in a chilled liquid coolant or by direct conduction from a solid coolant, and by pulsed electrical resistance heating. The liquid coolant can be static or moving. The solid coolant may be comprised of a single material or of multiple layers of varying materials. The methods and devices of the present teachings achieve dramatic increase in rates of heat transfer in comparison to prior art gas-phase heat removal methods.

Further, the present teachings greatly reduce the power and consumable supply requirements for 2DGC. In contrast to prior art, the devices of the present teachings can draw as little as a few tens of watts average electrical power, and eliminate the need for the 2DGC user to supply consumable gases for cooling the modulated column sections. The cooling system can take advantage of a closed loop flow (moving liquid coolant) or no flow (stationary liquid coolant or solid coolant), if desired.

It will be appreciated by a person of ordinary skill in the art that the present teachings can also be used for sample pre-concentration prior to GC analysis. This can be easily achieved, for example, by passing a continuous flow of the analyte gas through the modulated column section for some time, during which it is adsorbed into the cold stationary phase. Quickly heating the modulated column section, while directing the flow into a GC device, injects a much higher concentration of analyte into the column, so that the constituents are more easily detected at the outlet of the column(s).

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A thermal modulator device for coupling first and second chromatographic columns of a two-dimensional gas chromatography apparatus, the thermal modulator device comprising:
   a bath of a liquid coolant;
   an electrically conductive capillary immersed in the liquid coolant;
   and a power supply electrically coupled to the capillary and operable for controlled resistive heating of the capillary.

2. The thermal modulator device of claim 1, wherein the liquid coolant is moving.

3. The thermal modulator device of claim 1, wherein the liquid coolant comprises any one of ethylene glycol, or a mixture of ethylene glycol and water, or a dielectric silicone-based fluid.

4. The thermal modulator device of claim 2, further comprising a thermoelectric device operably connected to thermal modulator device for receiving and cooling the moving liquid coolant.

5. The thermal modulator device of claim 2, further comprising a pumping device operably coupled with thermal modulator device for pumping the moving liquid across the capillary.

6. A method for temperature modulation in gas chromatography, the method comprising:
   providing an electrically conductive capillary coupling first and second chromatographic columns of a two-dimensional gas chromatographer;
   immersing the capillary in a bath of a liquid coolant;
   chilling the capillary in the liquid coolant; and
   coupling the capillary to an electric power supply for resistive heating of the capillary.

7. The method of claim 6, further comprising pulsing the resistive heating.

8. The method of claim 6, further comprising moving the liquid coolant across the capillary.

* * * * *